(12) United States Patent
Trout et al.

(10) Patent No.: US 6,545,146 B1
(45) Date of Patent: Apr. 8, 2003

(54) LOWER ALKYL ALCOHOL RECOVERY FROM A STRIPPING MIXTURE

(75) Inventors: James Earl Trout, West Chester, OH (US); Gary Allen Busch, Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/582,747

(22) PCT Filed: Dec. 22, 1998

(86) PCT No.: PCT/US98/27275
§ 371 (c)(1),
(2), (4) Date: Jun. 30, 2000

(87) PCT Pub. No.: WO99/35152
PCT Pub. Date: Jul. 15, 1999

Related U.S. Application Data
(60) Provisional application No. 60/072,388, filed on Jan. 9, 1998.

(51) Int. Cl.$^7$ .............................. C07H 1/06; C07H 1/08
(52) U.S. Cl. ................... 536/127; 536/115; 536/119; 536/124; 554/1; 554/10; 554/12
(58) Field of Search .................. 536/115, 119, 536/120, 124, 127; 554/1, 10, 12

(56) References Cited

U.S. PATENT DOCUMENTS

| | | |
|---|---|---|
| 3,940,428 A * | 2/1976 | Connell et al. ............ 260/449.5 |
| 3,963,699 A | 6/1976 | Rizzi et al. |
| 4,238,403 A * | 12/1980 | Pinto ..................... 260/449.5 |
| 4,295,282 A | 10/1981 | Fox |
| 4,480,393 A | 11/1984 | Flink et al. |
| 4,517,360 A | 5/1985 | Volpenhein |
| 4,518,772 A | 5/1985 | Volpenhein |
| 4,861,613 A | 8/1989 | White et al. |
| 4,983,329 A | 1/1991 | Cooper |
| 5,043,438 A * | 8/1991 | Buter ..................... 536/119 |
| 5,152,812 A | 10/1992 | Kovach |
| 5,175,323 A | 12/1992 | Cooper |
| 5,231,199 A * | 7/1993 | Willemse ................. 554/174 |
| 5,273,772 A | 12/1993 | Cooper |
| 5,288,884 A | 2/1994 | Cooper |
| 5,298,637 A | 3/1994 | Cooper |
| 5,304,665 A | 4/1994 | Cooper et al. |
| 5,374,446 A | 12/1994 | Ferenz et al. |
| 5,387,429 A | 2/1995 | Cooper |
| 5,399,728 A | 3/1995 | Cooper |
| 5,399,729 A | 3/1995 | Cooper et al. |
| 5,427,815 A | 6/1995 | Ferenz |
| 5,446,843 A | 8/1995 | Fucito et al. |
| 5,512,313 A | 4/1996 | Cooper et al. |
| 5,516,544 A | 5/1996 | Sekula et al. |
| 5,589,217 A | 12/1996 | Mazurek |
| 5,597,605 A | 1/1997 | Mazurek |
| 5,603,978 A | 2/1997 | White et al. |
| 5,641,534 A | 6/1997 | White et al. |
| 5,648,483 A * | 7/1997 | Granberg et al. ........... 536/119 |

FOREIGN PATENT DOCUMENTS

| | | |
|---|---|---|
| WO | WO 97/22260 | 6/1997 |
| WO | WO 98/03526 | 1/1998 |
| WO | WO 98/03527 | 1/1998 |

* cited by examiner

Primary Examiner—James O. Wilson
Assistant Examiner—Patrick Lewis
(74) Attorney, Agent, or Firm—Karen F. Clark; Erich D. Hemm; Melody A. Jones

(57) ABSTRACT

Methods of removing a lower alkyl alcohol from a polyester mixture of polyol fatty acid polyester and lower alkyl alcohol comprise (a) contacting the polyester mixture with a stripping mixture comprising an inert stripping gas, up to about 10,000 ppm lower alkyl alcohol and up to about 2000 ppm oxygen, wherein at least a portion of the lower alkyl alcohol is transferred from the polyester mixture to the stripping mixture, thereby increasing the concentration of lower alkyl alcohol in the stripping mixture, and (b) separating the stripping mixture from the polyester mixture. The methods further comprise (c) compressing the stripping mixture to increase its pressure, (d) cooling the stripping mixture to reduce its temperature thereby condensing at least a first portion of the lower alkyl alcohol to a liquid, (e) separating condensed lower alkyl alcohol from the stripping mixture to reduce the amount of lower alkyl alcohol in the stripping mixture to a range of from about 1 ppm to about 10,000 ppm, and (f) directing the resulting stripping mixture to an expansion turbine in which the temperature and pressure of the stripping mixture are reduced. Energy resulting from the decrease in the stripping mixture temperature and pressure in the expansion turbine is used to compress the stripping mixture separated from the polyester mixture.

27 Claims, 1 Drawing Sheet

US 6,545,146 B1

LOWER ALKYL ALCOHOL RECOVERY FROM A STRIPPING MIXTURE

This application is a 371 of PCT/US98/27275 filed Dec. 22, 1998, which claims the benefit of provisional application No. 60/072,388 filed Jan. 9, 1998.

TECHNICAL FIELD

The present invention is directed to methods for removing lower alkyl alcohol from polyol fatty acid polyesters by contacting the polyol fatty acid polyester and lower alkyl alcohol mixture with a stripping mixture comprising an inert stripping gas, lower alkyl alcohol and oxygen. After such contact, the concentration of lower alkyl alcohol in the stripping mixture is increased. The invention is also directed to energy efficient methods for removing the lower alkyl alcohol from the stripping mixture by increasing the pressure and reducing the temperature of the stripping mixture so that a portion of the lower alkyl alcohol condenses to a liquid which can be more easily separated from the stripping mixture.

BACKGROUND OF THE INVENTION

There has been considerable interest in the use of certain polyol fatty acid polyesters as low or reduced calorie substitutes for fats and oils in foods. For example, non-absorbable, non-digestible sugar fatty acid esters or sugar alcohol fatty acid esters having at least four fatty acid ester groups, with each fatty acid having from 8 to 22 carbon atoms, have been used as partial or full fat substitutes in low calorie food compositions.

A number of different processes have been disclosed in the art for preparing these highly esterified polyol fatty acid polyesters, in particular sucrose polyesters. In general, a polyol, for example sucrose, is reacted with a fatty acid lower alkyl ester in the presence of a basic initiator catalyst to form a polyol fatty acid polyester. Emulsifiers, phase transfer catalysts and the like can be used to promote the reaction between the polyol and the fatty acid lower alkyl ester. Lower alkyl alcohol is a by-product of this reaction and its presence in the reaction mixture tends to slow the reaction's progression. Additionally, the lower alkyl alcohol is generally not a desired component in the polyol fatty acid polyester product. Thus, it is desirable to remove the lower alkyl alcohol from the polyol fatty acid polyester to both produce a purified polyol fatty acid polyester and to speed the reaction between a polyol and a fatty acid lower alkyl ester.

Moreover, oxygen is generally considered a poison in a transesterification reaction or in a mixture of a polyol fatty acid polyester and lower alkyl alcohol due to its tendency to oxidize reactants and products and to degrade the reaction catalyst. Hence, it is desirable to minimize the amount of oxygen which is added to a mixture of polyol fatty acid polyester and lower alkyl alcohol.

Lower alkyl alcohol can be removed from a polyol fatty acid polyester by sparging with an inert gas. This process is discussed in U.S. Pat. No. 4,518,772 to Volpenhein, U.S. Pat. No. 3,963,699 to Rizzi et al. and U.S. Pat. No. 4,517,360 to Volpenhein. These patents disclose a method of vacuum separation for the removal of the lower alkyl alcohol wherein inert gas sparging is used as a supplement to the vacuum removal of lower alkyl alcohol.

Processes for removing volatile organics from inert gas streams are generally known. For example, U.S. Pat. No. 4,295,282 to Fox discloses an open cycle heat pump system for recovering condensable solvents and/or heat from gas streams. This process is disclosed in conjunction with the removal of paint fumes and other volatile vapors from the gas stream. U.S. Pat. No. 4,480,393 to Flink et al. and U.S. Pat. No. 5,152,812 to Kovach also disclose processes for recovering condensable organic components from an inert gas stream.

Owing to the increased use of polyol fatty acid polyesters in food products and the like, there is a continuing need to improve the efficiency of and reduce the costs of manufacturing the polyol fatty acid polyesters. Specifically, there is a continuing need for fully integrated processes which are both efficient and economical and which can provide for removal of lower alkyl alcohol from a polyol fatty acid polyester mixture comprising a polyol fatty acid polyester and a lower alkyl alcohol.

SUMMARY OF THE INVENTION

It is an object of the present invention to provide improved methods for removing lower alkyl alcohol from a polyol fatty acid polyester mixture using a stripping mixture comprising an inert stripping gas, lower alkyl alcohol and oxygen and subsequently removing a portion of the lower alkyl alcohol from the stripping mixture, whereby the stripping mixture may be recycled for further use if desired.

It is an additional object of the present invention to provide such processes for removing a sufficient amount of the lower alkyl alcohol from the stripping mixture to allow the gas to be recycled for further contact with a polyol fatty acid polyester reaction mixture and/or polyester mixture containing lower alkyl alcohol.

In one embodiment, the present invention is directed to a method for removing lower alkyl alcohol from a polyester mixture which comprises polyol fatty acid polyester and lower alkyl alcohol. The polyester mixture is contacted by a stripping mixture comprising an inert stripping gas, up to about 10,000 ppm lower alkyl alcohol and up to about 2000 ppm oxygen. During the contact, at least a portion of the lower alkyl alcohol is transferred from the polyester mixture to the stripping mixture, thereby increasing the concentration of lower alkyl alcohol in the stripping mixture. The stripping mixture is then separated from the polyester mixture and the stripping mixture is compressed to increase its pressure. Additionally, the stripping mixture is cooled to condense at least a first portion of the lower alkyl alcohol to a liquid. Finally, condensed lower alkyl alcohol is separated from the stripping mixture to reduce the amount of lower alkyl alcohol in the stripping mixture to a range of from about 1 ppm to about 10,000 ppm, and the resulting stripping mixture is directed to an expansion turbine in which the temperature and pressure of the stripping mixture are reduced. The energy resulting from the decrease in the stripping mixture temperature and pressure in the expansion turbine is used to compress the stripping mixture separated from the polyester mixture. The resulting stripping mixture may optionally be used as a coolant in one or more heat exchangers to cool an additional quantity of stripping mixture separated from the reaction mixture.

In a preferred embodiment, the present invention comprises a method for removing a lower alkyl alcohol from a polyester mixture in a reaction mixture resulting from the reaction of polyol and fatty acid lower alkyl ester. The reaction mixture comprises reaction products including polyol fatty acid polyester and lower alkyl alcohol. The reaction mixture is contacted by a stripping mixture comprising an inert stripping gas, up to about 10,000 ppm lower alkyl alcohol and up to about 2,000 ppm oxygen. During the contact, at least a portion of the lower alkyl alcohol is transferred from the reaction mixture to the stripping mixture, thereby increasing the concentration of lower alkyl alcohol in the stripping mixture. The stripping mixture is then separated from the reaction mixture and the stripping mixture is compressed to increase its pressure. Additionally, the stripping mixture is cooled to condense at least a first portion of the lower alkyl alcohol to a liquid. Finally, a portion of the condensed first portion of lower alkyl alcohol is separated from the stripping mixture to reduce the amount of lower alkyl alcohol in the stripping mixture to a range of from about 1 ppm to about 10,000 ppm, and the resulting stripping mixture is directed to an expansion turbine in which the temperature and pressure of the stripping mixture are reduced. The energy resulting from the decrease in the stripping mixture temperature and pressure in the expansion turbine is used to compress the stripping mixture separated from the polyester mixture.

In another embodiment, the present invention comprises a method for synthesizing polyol fatty acid polyester. Specifically, a polyol is reacted with fatty acid lower alkyl ester to form a reaction mixture which comprises polyol fatty acid polyester and lower alkyl alcohol. The reaction mixture is contacted with a stripping mixture according to the methods described above.

The methods described herein provide the advantage of an integrated process for removing lower alkyl alcohol from a polyol fatty acid polyester mixture, condensing the alcohol to a liquid and separating the condensed alcohol from the stripping mixture, with significant energy recovery. Surprisingly, it has been found that to remove lower alkyl alcohol from a polyester mixture, an inert stripping gas which comprises up to about 10,000 ppm of lower alkyl alcohol can be used to obtain substantial removal of the lower alkyl alcohol from the polyester mixture. Moreover, in many polyester mixtures oxygen is considered a contaminant and it has been determined that the stripping mixtures of the present invention can comprise up to about 2,000 ppm oxygen without significantly degrading the reaction performance.

Additionally, the stripping mixture may subsequently be vented to the atmosphere or recycled for contact with further polyol fatty acid polyester. By using the cooled stripping mixture from which a portion of the lower alkyl alcohol has been condensed and separated as a coolant in at least one heat exchanger to cool an additional quantity of stripping mixture, additional energy and operational savings may be realized.

BRIEF DESCRIPTION OF THE DRAWING

The specification will be better understood from the following description taken in conjunction with the accompanying drawing in which.

DETAILED DESCRIPTION

Figure 1:
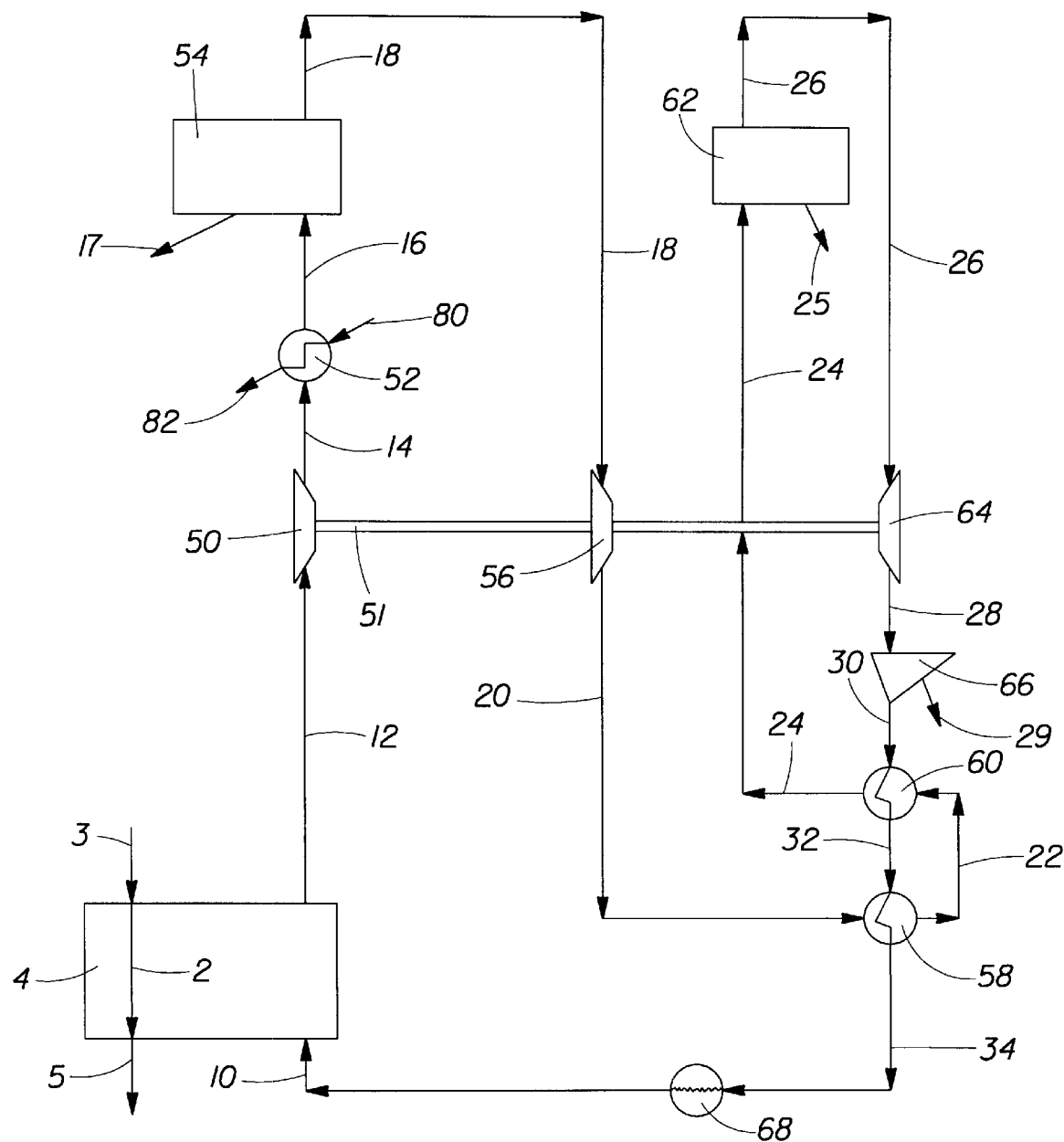
FIG. 1 is a schematic process flow diagram of a preferred embodiment of the present invention.

The present invention will now be described in detail with reference to specific embodiments. In accordance with the present invention, lower alkyl alcohol is removed from a mixture of polyol fatty acid polyester and the alcohol. Typically, a polyol is reacted with a fatty acid lower alkyl ester to produce a polyol fatty acid polyester by transesterification of the polyol, with the formation of a lower alkyl alcohol as a by-product. During the transesterification reaction of polyol to form polyol fatty acid polyester, the production of lower alkyl alcohol by-product shifts the reaction equilibrium and slows the reaction. To achieve a high degree of transesterification, i.e., to esterify as many hydroxyl groups of the polyol as possible, it is therefore advantageous to remove the lower alkyl alcohol from the reaction mixture so that the reaction of the polyol does not reach equilibrium prior to obtaining the desired level of transesterification of the polyol. As used herein, "reaction mixture" is intended to include a mixture comprising polyol fatty acid polyester and lower alkyl alcohol. The reaction mixtures described herein can comprise numerous unreacted reactants, catalyst and by-products of side reactions which occur during the transesterification reaction. Moreover, as used herein, "polyester mixture" is intended to include mixtures comprising polyol fatty acid polyester and lower alkyl alcohol from any source and it is understood that the reaction mixture defined above is a subset of a polyester mixture as defined herein.

Polyol fatty acid polyesters produced by methods other than transesterification may also contain lower alkyl alcohol, and it is often desirable to remove the lower alkyl alcohol from the polyol fatty acid polyester to obtain a purified product. Hence, while the removal of lower alkyl alcohol is described herein primarily in conjunction with a reaction mixture, it is understood that the lower alkyl alcohol removal methods disclosed herein are applicable to the removal of lower alkyl alcohol from polyol fatty acid polyesters regardless of the source of the polyol fatty acid polyester.

As used herein, the term "polyol" is intended to include any aliphatic or aromatic compound containing at least two free hydroxyl groups. Suitable polyols can be selected from the following classes: saturated and unsaturated straight and branch chain linear aliphatics; saturated and unsaturated cyclic aliphatics, including heterocyclic aliphatics; or mononuclear or polynuclear aromatics, including heterocyclic aromatics. Carbohydrates and non-toxic glycols are preferred polyols. Monosaccharides suitable for use herein include, for example, mannose, galactose, arabinose, xylose, ribose, apiose, rhamnose, psicose, fructose, sorbose, tagatose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. Natural sugar alcohols which are suitable for use herein are sorbitol, mannitol, and galactitol.

Particularly preferred classes of materials suitable for use herein include the monosaccharides, the disaccharides and sugar alcohols. Preferred unesterified polyols include glucose, fructose, glycerol, polyglycerols, sucrose, zylotol, and sugar ethers. A particularly preferred polyol is sucrose. Preferred unesterified polyols also include alkoxylated polyols such as alkoxylated glycerol, alkoxylated polyglycerols, sorbitol alkoxylated glycerines, alkoxylated polysaccharides, and linked alkoxylated polyols such as linked alkoxylated glycerins. Polyols may be alkoxylated with $C_3$–$C_6$ epoxides, such as propylene oxide, butylene oxide, isobutylene oxide, and pentene oxide, to produce epoxide-extended polyols having an epoxylation index minimum of at least about 2, preferably in the range of from about 2 to about 8, as described in U.S. Pat. No. 4,816,613, incorporated herein by reference. Polyols may be also alkoxylated with an epoxide, preferably a $C_3$–$C_{10}$ 1,2-alkylene oxide, in the presence of a ring-opening polymerization catalyst, as described in U.S. Pat. Nos. 5,399,729 and 5,512,313, incorporated herein by reference.

Suitable alkoxylated polyols for use herein are described in U.S. Pat. Nos. 4,983,329; 5,175,323; 5,288,884; 5,298,637; 5,362,894; 5,387,429; 5,446,843; 5,589,217; 5,597,605; 5,603,978 and 5,641,534, all incorporated herein by reference. Suitable alkoxylated polyols include alkoxylated sugar alcohols, alkoxylated monosaccharides, alkoxylated disaccharides, alkoxylated polysaccharides, alkoxylated $C_2$–$C_{10}$ aliphatic diols, and alkoxylated $C_3$–$C_{12}$ aliphatic triols. Preferred alkoxylated $C_3$–$C_{12}$ aliphatic triols are alkoxylated glycerols, more preferred are propoxylated glycerols, and particularly preferred are propoxylated glycerols having from about 3 to about 21 moles of propylene oxide per mole glycerol. Preferred alkoxylated polysaccharides are alkoxylated polysaccharides containing anhydromonosaccharide units, while more preferred are propoxylated polysaccharides containing anhydromonosaccharide units, as described in U.S. Pat. No. 5,273,772, incorporated herein by reference. Preferred linked alkoxylated glycerins include those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

As used herein the term "polyol fatty acid polyester" is intended to include any polyol, as defined herein, which has two or more of its hydroxyl groups esterified with fatty acid groups. Suitable polyol fatty acid polyesters include sucrose polyesters having on average at least four, preferably at least about five, ester linkages per molecule of sucrose; the fatty acid chains preferably have from about eight to about twenty-four carbon atoms. Other suitable polyol fatty acid polyesters are esterified linked alkoxylated glycerins, including those comprising polyether glycol linking segments, as described in U.S. Pat. No. 5,374,446, incorporated herein by reference, and those comprising polycarboxylate linking segments, as described in U.S. Pat. Nos. 5,427,815 and 5,516,544, incorporated herein by reference; more preferred are those described in U.S. Pat. No. 5,516,544.

Additional suitable polyol fatty acid polyesters are esterified epoxide-extended polyols of the general formula P(OH)$_{A+C}$ (EPO)$_N$ (FE)$_B$ wherein P(OH) is a polyol, A is from 2 to about 8 primary hydroxyls, C is from about 0 to about 8 total secondary and tertiary hydroxyls, A+C is from about 3 to about 8, EPO is a $C_3$–$C_6$ epoxide, N is a minimum epoxylation index average number, FE is a fatty acid acyl moiety and B is an average number in the range of greater than 2 and no greater than A+C, as described in U.S. Pat. No. 4,861,613 and EP 0324010 A1, incorporated herein by reference. The minimum epoxylation index average number has a value generally equal to or greater than A and is a number sufficient so that greater than about 95% of the primary hydroxyls of the polyol are converted to secondary or tertiary hydroxyls. Preferably the fatty acid acyl moiety has a $C_7$–$C_{23}$ alkyl chain.

Preferred esterified epoxide-extended polyols for use herein include esterified propoxylated glycerols prepared by reacting a propoxylated glycerol having from 2 to about 100 oxypropylene units per glycerol with $C_{10}$–$C_{24}$ fatty acids or with $C_{10}$–$C_{24}$ fatty acid esters, as described in U.S. Pat. Nos. 4,983,329 and 5,175,323, respectively, both incorporated herein by reference. Also preferred are esterified propoxylated glycerols prepared by reacting an epoxide and a triglyceride with an aliphatic polyalcohol, as described in U.S. Pat. No. 5,304,665, incorporated herein by reference, or with an alkali metal or alkaline earth salt of an aliphatic alcohol, as described in U.S. Pat. No. 5,399,728, incorporated herein by reference. More preferred are acylated propylene oxide-extended glycerols having a propoxylation index of above about 2, preferably in the range of from about 2 to about 8, more preferably about 5 or above, wherein the acyl groups are $C_8$–$C_{24}$, preferably $C_{14}$–$C_{18}$, compounds, as described in U.S. Pat. Nos. 5,603,978 and 5,641,534, both incorporated herein by reference. Particularly preferred are fatty acid-esterified propoxylated glycerols which exhibit a sharp melt before about 92 F. (33 C.) and have a dilatomeric solid fat index at 92 F. (33 C.) of less than about 30, as described in WO 97/2260, or which have a dilatomeric solid fat index of at least about 50 at 70 F. (21 C.) and at least about 10 at 98.6 F. (37 C.), as described in U.S. Pat. Nos. 5,589,217 and 5,597,605, both incorporated herein by reference.

Other suitable esterified epoxide-extended polyols include esterified alkoxylated polysaccharides. Preferred esterified alkoxylated polysaccharides are esterified alkoxylated polysaccharides containing anhydromonosaccharide units. more preferred are esterified propoxylated polysaccharides containing anhydromonosaccharide units, as described in U.S. Pat. No. 5,273,772, incorporated herein by reference.

In the transesterification of polyol in accordance with the present invention, the desired product preferably is a polyol fatty acid polyester wherein at least half of the hydroxyl groups of the polyol are replaced with fatty acid esters. When the polyol is sucrose, four or more of the hydroxyl groups are desirably esterified. Even more preferably, the desired product is a polyol fatty acid polyester wherein all of the hydroxyl groups are transesterified. As each hydroxyl group of a polyol is transesterified, a molecule of lower alkyl alcohol is normally produced. Thus, the reaction mixture comprises, among other components, the desired polyol fatty acid polyester and the lower alkyl alcohol.

To remove the lower alkyl alcohol from a reaction mixture as described herein, a stripping mixture comprising an inert stripping gas, up to about 10,000 ppm, more preferably up to about 3,000 ppm, lower alkyl alcohol and up to about 2000 ppm is utilized oxygen. Surprisingly, it has been found that a stripping mixture as defined herein which comprises up to about 10,000 ppm of a lower alkyl alcohol, can be use to remove lower alkyl alcohol from a polyester mixture. Moreover, the stripping mixtures defined herein can comprise up to about 2000 ppm of oxygen which can be a contaminant in a polyester mixture. A preferred inert stripping gas for use in the present invention is nitrogen gas. However, other gases which are inert with respect to the polyol fatty acid polyester mixture, and in which the lower alkyl alcohol by-product is soluble can be utilized. Other inert stripping gases acceptable for use with the present invention include hexane and other aliphatic hydrocarbons.

To effect removal of the lower alkyl alcohol from a polyester mixture the stripping mixture is contacted with the polyester mixture. The contact can take place, for example, in a reaction vessel or any other appropriate vessel wherein the stripping mixture can contact the polyester mixture. The stripping mixture can be fed co-current to the polyol fatty acid polyester and lower alkyl alcohol mixture, or referably the stripping mixture can be fed countercurrent to the polyester mixture.

For a reaction mixture, it is preferable to contact the reaction mixture in the vessel where the reaction occurs. One preferred method for producing the polyol fatty acid polyesters of the present invention is to provide a vertical multi-stage column for reacting the polyol and the fatty acid lower alkyl ester wherein the reaction components are fed into the top of the column and are allowed to flow through the column to the bottom where the product stream is removed. The stripping mixture is fed into the bottom of the column, bubbling through the column and exiting from the top of the column. One such contactor 4 is schematically shown in FIG. 1.

The present invention can be better understood by reference to FIG. 1 which is a schematic representation of one method according to the present invention. Specifically, FIG. 1 illustrates a method wherein the polyol fatty acid polyester and lower alkyl alcohol mixture 2 is provided in a contactor 4 where the mixture 2 contacts a stripping mixture supplied via inlet 10. The mixture 2 of polyol fatty acid polyester and lower alkyl alcohol can be directed to the contactor 4 via an inlet stream 3. Alternatively, the contactor 4 can be a reaction vessel or the like in which the polyol fatty acid polyester-lower alkyl alcohol mixture is formed, for example, from polyol and fatty acid lower alkyl ester supplied to the contactor 4 via one or more reactant inlet streams 3. Exiting the contactor 4 is a stream 5 of polyol fatty acid polyester wherein a portion of lower alkyl alcohol has been removed by the stripping mixture supplied via inlet 10. Also exiting the contactor 4 is a stream 12 which comprises the stripping mixture with an increased concentration of lower alkyl alcohol. As shown in FIG. 1, the stripping mixture supplied via inlet 10 is fed counter-current to the polyol fatty acid polyester outlet stream 5, i.e., inlet 10 introduces the stripping mixture at or near the bottom of the contactor 4 and the stripping mixture is allowed to bubble through the polyester mixture 2 and exit the top of the contactor 4 while the polyol fatty acid polyester-lower alkyl alcohol mixture having a reduced lower alkyl alcohol content is preferably removed from the bottom of the contactor 4 via the stream 5. As can be appreciated, the amount of the stripping mixture introduced into the contactor 4 can vary significantly, depending upon, for example, the rate at which lower alkyl alcohol is produced or is present in the polyol fatty acid polyester and the amount of lower alkyl alcohol which is to be removed.

A preferred range for the ratio of stripping mixture supplied via inlet 10 to the polyol fatty acid polyester-lower alkyl alcohol mixture 2 is from about 0.1:1 to about 10:1, more preferably from about 0.5:1 to about 10:1, by weight. A further preferred range is from about 1:1 to about 5:1 stripping mixture to polyester mixture by weight. The inlet temperature of the stripping mixture is preferably close to that of the polyester mixture 2. However, as can be appreciated, due to the low thermal capacitance of gas, the temperature of the stripping mixture will rapidly equilibrate to the temperature of the liquid stream containing the mixture of polyol fatty acid polyester and the lower alkyl alcohol 2. Moreover, the contactor 4 can be cooled and/or heated, as appropriate, to maintain the desired temperature and to insure that the temperature of stripping mixture reaches the temperature of the polyester mixture 2.

The contactor 4 can be operated at a variety of pressures, but atmospheric or slightly elevated pressures, up to about 2500 mm Hg, are preferred. As can be appreciated, subjecting contactor 4 to a vacuum or subatmospheric pressures may promote the removal of the stripping mixture, which is in the form of a vapor or gas, via outlet 12, from the liquid polyester mixture 2. However, use of subatmospheric pressures promotes the introduction of air which can be drawn into contactor 4 through cracks, leaks or other openings in the contactor. The introduction of surrounding air to contactor 4 is undesirable because air contains an appreciable concentration of oxygen which is considered a poison to most polyester mixtures described herein. More specifically, oxygen is known to poison the catalyst used to promote the transesterification of a polyol and a lower alkyl methyl ester to form a polyol fatty acid ester. Additionally, oxygen can promote side reactions which compete with both reactants and products in a transesterification reaction which forms polyol fatty acid polyester. Both poisoning of the catalyst and promoting side reactions can cause a degradation of the reaction performance. Moreover, oxygen can serve to degrade the desired polyol fatty acid polyester in a polyester mixture. Hence, it is especially preferred that the stripping mixture, for example stream 10 entering contactor 4, have a concentration of oxygen of up to about 2000 parts per million. It is often impractical and uneconomical to reduce the concentration of oxygen in a stripping mixture below about 1 part per million. However, often it is not necessary to remove any oxygen from the stripping mixture after it exits the contactor because an appreciable amount of oxygen can be consumed during contact with the polyester mixture as discussed above. Thus, an especially preferred range of oxygen in stripping mixture 10 is between about 1 ppm and about 2000 ppm.

In contactor 4, at least a portion of lower alkyl alcohol is transferred from the polyester mixture to the stripping mixture. Thus, the concentration of lower alkyl alcohol in the stripping mixture exiting via stream 12 has a higher concentration of lower alkyl alcohol than the stripping mixture entering contactor 4 via stream 10. After the stripping mixture exits the contactor 4, it is fed through process equipment which increase the pressure and reduces the temperature of the stripping mixture, thereby causing at least a portion and preferably essentially all of the lower alkyl alcohol to condense into a liquid state. Those process steps are described in detail below.

After exiting contactor 4, a demister (not shown) and/or chiller (not shown) can be used to remove a portion of the liquid droplets which may be entrained in the stripping mixture in line 12 and to reduce the temperature of the stripping mixture in line 12, respectively. To increase the pressure of the stripping mixture, any appropriate pressurizing means can be used, for example, compressors 50 and 56 shown schematically in FIG. 1. The pressure of the stripping mixture exiting compressor 50 via stream 14 can be raised up to about 1700 mm Hg and preferably up to about 2100 mm Hg. Compatibility with the stripping mixture is necessarily required for any compressor used and each compressor should be properly sized to handle the flow rates of stripping mixtures in lines 12 and 18.

One or more heat exchangers, indicated as 52, can be used to reduce the temperature of the stripping mixture in line 14 after it exits the compressor 50. Any of a variety of commonly available heat exchangers can be used, provided that they are compatible with the stripping mixture. Heat exchangers in general, and heat exchangers suitable for use in the present invention, require a coolant, provided via stream 80. The temperature of the stripping mixture in line 14 is lowered as it flows in heat exchange relation with the coolant. The coolant is typically fed counter-current to the stripping mixture in line 14, although co-current flow is also acceptable. Cold water, glycols and other coolants known to the art are acceptable coolants for use with the methods described herein. Necessarily, the temperature of the coolant in stream 80 is increased as it flows through and exits the heat exchanger via stream 82. One skilled in the art would recognize that the location and number of heat exchangers and compressors are a design consideration which can be varied without diverging from the methods of the present invention.

The increase in pressure and decrease in temperature of stripping mixture 16 can cause at least a portion of the lower alkyl alcohol from the mixture to condense to a liquid. Alternatively, or in addition to condensing a portion of the lower alkyl alcohol contained in stream 16, vaporized polyol fatty acid polyester contained in stream 16 can be condensed as the stripping mixture is passed through the heat exchanger 52. The temperature and pressure necessary to condense the lower alkyl alcohol will depend primarily on the type and concentration of lower alkyl alcohol being stripped from the polyol fatty acid polyester. For example, preferred fatty acid lower alkyl esters for use in the production of polyol fatty acid polyester of the present invention are fatty acid methyl esters. When fatty acid methyl esters react with polyol to remove a hydroxyl group from the polyol, replacing it with a fatty acid ester, methanol is produced. Thus, methanol would be stripped from the polyol fatty acid polyester mixture by the stripping mixture. At atmospheric pressure, the boiling point of methanol is approximately 64 C. The temperature of the stripping mixture must be reduced to at least below about 64 C. to condense some of the methanol at atmospheric pressure. However, because the stripping mixture is compressed by the methods described herein, i.e, the pressure of the gas mixture is increased, the boiling point of the alcohol is subsequently raised.

As will be appreciated by those skilled in the art, condensation of a vapor to its liquid form begins at the vapor's boiling point, but often not all of the vapor will condense at that temperature. Therefore, it is preferred, and often necessary, to reduce the temperature of the stripping mixture to levels significantly below the boiling point of the lower alkyl alcohol to remove an appreciable quantity of alcohol from the stripping mixture. It is preferred to remove at least about 90% by weight, and more preferably 99% by weight, of the alcohol from the stripping mixture.

To ensure essentially complete removal of the lower alkyl alcohol from the stripping mixture, the temperature of the stripping mixture is preferably reduced to below about −35 C. and more preferably to below about −65 C. so that essentially all of the lower alkyl alcohol is condensed to a liquid. Condensing "essentially all" of the lower alkyl alcohol means condensing greater than about 99% by weight of the lower alkyl alcohol present in the stripping mixture. Preferably, however, for the stripping mixture to be suitable for further contact with a polyester mixture, the amount of lower alkyl alcohol should be reduced to below about 10,000 ppm, more preferably to below about 3000 ppm. Even more preferably, the lower alkyl alcohol in the striping mixture is reduced to below about 200 ppm and most preferably below about 20 ppm before the stripping mixture is recycled for further contact with the polyester mixture. As can be appreciated, to reduce the amount of lower alkyl alcohol in the stripping mixture to below about 1 ppm may be costly and/or impractical. Hence, a preferred range of lower alkyl alcohol in the stripping mixture prior to contact with a polyester mixture is between about 1 ppm and 10,000 ppm of lower alkyl alcohol.

Separation of the lower alkyl alcohol condensed liquid from the stripping mixture in stream 16 can be accomplished by any appropriate means, as shown schematically by separator 54, wherein the stripping mixture containing condensed lower alkyl alcohol flows into the separator 54 via the stream 16. The collected liquid alcohol is removed from the separator 54, via stream 17, as the stripping mixture flows through the separator. The stripping mixture leaves the separator 54 via a stream 18 and is directed to a compressor 56 for additional compression up to about 3700 mm Hg, in the preferred embodiment of the present invention shown in FIG. 1. Examples of suitable separators for use herein include, but are not limited to, fiber mist eliminator, impingement separator, gravity separator, and/or mesh pad separator.

After the stripping mixture is further compressed, it exits the compressor 56 via a stream 20. In the preferred embodiment of the present invention shown in FIG. 1, the stripping mixture in stream 20 is directed to two heat exchangers, 58 and 60, wherein the coolant streams, 30 and 32 of the heat exchanger comprise stripping mixture which has been cooled by expansion through an expansion turbine 64. More specifically, the stripping mixture in stream 20 exiting the compressor 56 passes through the heat exchanger 58 and exits via a stream 22. The stripping mixture in stream 22 is then directed to a heat exchanger 60 where it exits via stream 24. The striping mixture in stream 24, after having been chilled to a temperature preferably below about −35 C. to condense a second portion of the lower alkyl alcohol, is fed to a separator 62 wherein at least a portion of the second condensed portion of lower alkyl alcohol is removed from the stripping mixture as liquid alcohol stream 25. Suitable separators include, for example, fiber mist eliminator, impingement separator, gravity separator, and/or mesh pad separator. The stripping mixture exits separator 62 via a stream 26 and is then passed through the expansion turbine 64. The striping mixture exits the expansion turbine 64 via a stream 28.

The expansion turbine 64 generates energy from the expanding stripping mixture. Specifically, the pressurized stripping mixture drives the turbine 64, thus, reducing the pressure, and subsequently reducing the temperature, of the stripping mixture wherein the reduction in pressure and temperature is transformed into mechanical energy. Preferably, the temperature and pressure of the stripping mixture contained in stream 26 are reduced to below about −50 C. and to below about 1500 mm Hg, and more preferably to below about −75 C. and to below about 1800 mm Hg. Energy generated by the reduction in pressure and temperature is advantageously used to compress the stripping mixture separated from the polyol fatty acid polyester. A shaft 51 can be connected to the turbine 64 so that the stripping mixture 26 entering the expansion turbine 64 drives the shaft 51 wherein the rotating shaft can provide power for other mechanical apparatuses, for example, a portion of power to drive the compressors 50 and 56 which are used to compress the stripping mixture in the streams 12 and 18, respectively. The increase in the pressure of the stripping mixture streams 12 and 18 in compressors 50 and 56, driven by expansion turbine 64, will not be equal to the pressure drop of stripping mixture 26 passing through expansion turbine 64 as some energy will necessarily be lost to friction and other energy losses. One skilled in the art will recognize that the configuration of one expansion turbine connected to two compressors by a common shaft is a matter of design preference and other configurations, for example a plurality of expansion turbines and one compressor connected by a common shaft, are possible and will be apparent to those skilled in the art.

While in the expansion turbine 64, both the temperature and pressure of the stripping mixture are reduced. By this method, the stripping mixture in stream 28 can then be utilized as the coolant in heat exchangers 60 and 58. The stripping mixture in stream 28 is preferably passed through a demister 66 wherein fine droplets of entrained liquid are physically separated from the stripping mixture which exits the demister 66 as liquid stream 29. A commercially available Brownian fiber demister is preferred for use with the methods described herein, although other demisters may also be employed. The stripping mixture exits the demister 66 via a stream 30. The stripping mixture in stream 30 serves as the coolant for the heat exchanger 60 and therefore the temperature of the stripping mixture in stream 30 is increased as it exits the exchanger 60 via a stream 32. The stripping mixture in stream 32 is utilized as the coolant for the heat exchanger 58 wherein the temperature of the stripping mixture is increased. The stripping mixture exits heat exchanger 58 via a stream 34.

After flowing through the heat exchangers 60 and 58, the stripping mixture in stream 34 can be vented to the atmosphere via a vent (not shown). Venting a portion of the stripping mixture, for example 1.0–10%, and replacing it with an inert stripping gas which is relatively free of oxygen, is often desirable to reduce the amount of oxygen in the stripping mixture prior to further contact with a polyester mixture. Alternatively, or in addition, the stripping mixture can be recycled to the polyol fatty acid polyester contactor for further contact with the polyester or reaction mixture and/or recycled to the stripping mixture in stream 12 in order to reduce the temperature of the stripping mixture in stream 12. Any combination of these three uses for the stripping mixture in stream 34 can be employed. From an economic point of view, it is desirable to minimize the amount of the stripping mixture 34 which is vented to the atmosphere so as to maintain steady state flow conditions. If the stripping mixture in stream 34 is intended for recycle for further contact with a polyester mixture, any stripping mixture which is vented to the atmosphere must be replaced by an essentially equal amount of stripping mixture to maintain steady state flow through the contactor 4.

EXAMPLE I

The foregoing Detailed Description can be better understood by reference to the following example wherein Table I sets forth preferred process parameters according to one embodiment of the present invention. The stream numbers, 10 through 34, correspond with the streams shown in FIG. 1. Specifically, the stripping mixture in stream 10 which is fed into the contactor 4 to contact a polyester mixture 2 comprises primarily nitrogen and 18 ppm methanol. As can be seen, the stripping mixture which exits contactor 4 via stream 12 contains over 1200 lbs/hr of methanol in addition to the nitrogen. An inline cooler (not shown) and demister (not shown) are utilized to reduce the temperature of stripping mixture in stream 12 to about 110 F. (45 C.) while removing a portion of any liquid droplets which become entrained in the vapor phase of the stripping mixture. The stripping mixture in stream 12 is then compressed from a pressure of 0.9 psig to about 24.41 psig in the compressor 50 which simultaneously increases the temperature of the stripping mixture to about 320 F. (160 C.). The stripping mixture exits compressor 50 via the stream 14.

The temperature of the stripping mixture in stream 14 is reduced in heat exchanger 52 to about 110 F. (45 C.) and the stripping mixture exits the compressor 50 via the stream 16. The stripping mixture from stream 16 is passed through separator 54 which at a temperature of 110 F. (45 C.) removes essentially no methanol from the stripping mixture. However, polyol fatty acid polyester and other organic materials having boiling points higher than methanol may be condensed and separated from the stripping mixture via the separator 54. The stripping mixture exits separator 54 via stream 18 and is further compressed in compressor 56 to a pressure of about 55.3 psig, which increases the temperature of stripping mixture 18 to about 250 F. (120 C.). The temperature of stripping mixture in stream 20 is then reduced in heat exchanger 58, and the stripping mixture exits via stream 22 at a temperature of about 78 F. (25 C.). Subsequently, the temperature of the stripping mixture in stream 22 is reduced as it is passed through heat exchanger 60, and the stripping mixture exits via stream 24 at a temperature of about –49 F. (–45 C.).

Stream 24 is then passed through separator 62 wherein approximately 1200 lb/hr of liquid methanol is removed from the stripping mixture which exits separator 62 via liquid stream 27. This represents a removal rate of approximately 98% of the methanol in separator 62. As can be seen, the stripping mixture in stream 26 exiting separator 62 contains approximately 300 ppm of methanol. As can be appreciated, the pressure of stream 26 is slightly lower than stream 20 due to frictional losses incurred as the stripping mixture is passed through the two heat exchangers and the separator. The stripping mixture 26 is then expanded in expansion turbine 64 as described above to decrease both the temperature and the pressure of the stripping mixture in stream 26 to about –102 F. (–75 C.) and about 20.6 psig. The stripping mixture exits expansion turbine 64 via stream 28.

At this point in the process, an additional amount of methanol condenses, but due to the extremely low concentration of methanol it is often difficult to remove it in a standard separator. Hence, it is preferred to use a fiber mist eliminator as the demister 66 wherein entrained droplets of liquid can be physically separated from the gaseous stream, i.e., the stripping mixture in stream 28, and then collected and removed as a liquid, for example via stream 29. The stripping mixture which exits demister 66 via stream 30 contains approximately 18 parts per million of methanol which represents approximately 0.1% of the original amount of methanol removed from the polyester mixture. The stripping mixture in stream 30 is utilized as the coolant in heat exchanger 60 to cool the stripping mixture in stream 22 as described above. The temperature of the stripping mixture in stream 30 is increased in heat exchanger 60 from about –102 F. (–75 C.) to about 50 F. (10 C.), and exits via stream 32. The stripping mixture in stream 32 is used as the coolant for heat exchanger 58 to cool the stripping mixture in stream 20 wherein the temperature of the stripping mixture in stream 32 is increased from about 50 F. (10 C.) to about 234 F. (110 C.) and exits via stream 34. An optional heater 68 which increases the temperature of the stripping mixture in stream 34 from about 234 F. (110 C.) to about 275 F. (135 C.) is shown. Heater 68 can be an electrical heater or an additional heat exchanger and is utilized to prepare the stripping mixture in stream 10 for further contact with a polyester mixture in contactor 4.

TABLE I

| | Stream | | | | |
| --- | --- | --- | --- | --- | --- |
| | 10 | 12 | 14 | 16 | 18 |
| Methanol, lb/hr | 1.6 (18 ppm) | 1267.6 | 1267.6 | 1267.6 | 1267.6 |
| Nitrogen, lb/hr | 89697.1 | 89698.4 | 89698.4 | 89698.4 | 89698.4 |
| Temp., F. | 275 | 110 | 320 | 110 | 110 |

TABLE I-continued

| | | | | | |
|---|---|---|---|---|---|
| Pressure, psig | 15.30 | 0.90 | 24.41 | 24.00 | 22.41 |
| Density, lb/ft³ | 0.11 | 0.07 | 0.13 | 0.14 | 0.17 |

| | Stream | | | | |
|---|---|---|---|---|---|
| | 20 | 22 | 24 | 26 | 25 |
| Methanol, lb/hr | 1267.6 | 1267.6 | 1267.6 | 26.2 (300 ppm) | 1241.4 |
| Nitrogen, lb/hr | 89698.4 | 89698.4 | 89697.2 | 89697.2 | 1.3 |
| Temp., F. | 250 | 70 | 49 | −49 | −49 |
| Pressure, psig | 55.30 | 51.90 | 49.80 | 49.00 | 49.00 |
| Density, lb/ft³ | 0.26 | 0.33 | 0.41 | 0.40 | 53.10 |

| | Stream | | | | |
|---|---|---|---|---|---|
| | 28 | 30 | 29 | 32 | 34 |
| Methanol lb/hr | 26.2 (300 ppm) | 1.6 (18 ppm) | 24.6 | 1.6 (18 ppm) | 1.6 (18 ppm) |
| Nitrogen lb/hr | 89697.2 | 89697.1 | 0.0 (600 ppm) | 89697.1 | 89697.1 |
| Temp. F. | −102 | −102 | −102 | 50 | 234 |
| Pressure psig | 20.60 | 20.10 | 20.10 | 18.00 | 15.90 |
| Density lb/ft³ | 0.26 | 0.25 | 54.65 | 0.17 | 0.12 |

Having shown and described the preferred embodiments of the present invention, further adaptations of the methods described herein can be accomplished by appropriate modifications by one of ordinary skill in the art without departing from the scope of the present invention. Several of these potential modifications have been mentioned, and others will be apparent to those skilled in the art. For example, while two compressors are shown processing the stripping mixture, one compressor or more than two compressors can be used. Moreover, as discussed above, the number and placement of heat exchangers can be varied and while it is envisioned that the stripping mixture will be reduced to a very low temperature, i.e., −35 C. or more, it is understood that the methods of removing lower alkyl alcohol from a stripping mixture can be accomplished at higher temperatures, although less alcohol may be removed. Accordingly, the scope of the present invention should be considered in terms of the following claims and understood not to be limited to the drawings of the processes and methods shown and described in the specification and drawings.

What is claimed is:

1. A method of removing a lower alkyl alcohol from a polyester mixture comprising polyol fatty acid polyester and lower alkyl alcohol, the method comprising the steps of:
   (a) contacting the polyester mixture with a stripping mixture comprising an inert stripping gas, up to about 10,000 ppm lower alkyl alcohol and up to about 2,000 ppm oxygen, wherein at least a portion of the lower alkyl alcohol is transferred from the polyester mixture to the stripping mixture, thereby increasing the concentration of lower alkyl alcohol in the stripping mixture,
   (b) separating the stripping mixture from the polyester mixture,
   (c) compressing the stripping mixture to increase its pressure,
   (d) cooling the stripping mixture to reduce its temperature, thereby condensing at least a first portion of the lower alkyl alcohol to a liquid,
   (e) separating at least a portion of the condensed lower alkyl-alcohol from the stripping mixture to reduce the amount of lower alkyl alcohol in the stripping mixture to a range of from about 1 ppm to about 10,000 ppm, and
   (f) directing the resulting stripping mixture to an expansion turbine in which the temperature and pressure of the stripping mixture are reduced,
   wherein energy resulting from the decrease in the stripping mixture temperature and pressure in the expansion turbine is used to compress the stripping mixture separated from the polyester mixture.

2. The method according to claim 1, wherein after step (e) but before step (f) a second portion of lower alkyl alcohol is condensed in the stripping mixture and condensed lower alkyl alcohol is separated from the stripping mixture.

3. The method according to claim 1, wherein in step (d) the stripping mixture is passed through at least two heat exchangers having a coolant flowing therethrough which reduces the temperature of the stripping mixture to less than about −35° C.

4. The method according to claim 3, wherein at least one of the heat exchangers comprises a water coolant which enters the heat exchanger at a temperature below about 100° F.

5. The method according to claim 3, wherein the stripping mixture exiting the expansion turbine is used as the coolant in at least one of the heat exchangers.

6. The method according to claim 1, wherein the stripping mixture exiting the expansion turbine is recycled for contact with a polyester mixture comprising polyol fatty acid polyester and lower alkyl alcohol.

7. The method according to claim 2, wherein after the condensed second portion of lower alkyl alcohol is removed from the stripping mixture, the stripping mixture is recycled for contact with a polyester mixture comprising polyol fatty acid polyester and lower alkyl alcohol.

8. The method according to claim 1, wherein the lower alkyl alcohol is methanol.

9. The method according to claim 1, wherein the polyol fatty acid polyester is a sucrose fatty acid polyester.

10. The method according to claim 1, wherein the expansion turbine is mechanically linked to a plurality of compressors and the energy generated by the decrease in the stripping mixture temperature and pressure in the expansion turbine is transferred to the plurality of compressors to increase the pressure of the stripping mixture after it is separated from the polyester mixture.

11. The method according to claim 2, wherein after the condensed second portion of lower alkyl alcohol is removed from the stripping mixture, at least a portion of the stripping mixture is vented to the atmosphere.

12. The method according to claim 1, wherein the stripping mixture has a concentration of less than about 200 ppm of lower alkyl alcohol after the condensed first portion of lower alkyl alcohol has been separated from the stripping mixture.

13. The method according to claim 1, wherein greater than about 99% of the lower alkyl alcohol transferred from the polyester mixture to the stripping mixture is removed from the stripping mixture when the condensed first portion of lower alkyl alcohol is separated from the stripping mixture.

14. The method according to claim 1, wherein in step (a) the inert gas is nitrogen.

15. The method according to claim 7, wherein before the stripping mixture is recycled for contact with the polyester mixture, at least a portion of the stripping mixture is diverted and combined with the separated stripping mixture from step (b).

16. A method of removing a lower alkyl alcohol from a reaction mixture resulting from a transesterification reaction of a polyol and a fatty acid lower alkyl ester, the reaction mixture comprising a polyol fatty acid polyester and the lower alkyl alcohol, the method comprising:

contacting the reaction mixture with a stripping mixture comprising an inert stripping gas, up to about 10,000 ppm lower alkyl alcohol and up to about 2,000 ppm oxygen, wherein at least a portion of the lower alkyl alcohol is transferred from the reaction mixture to the stripping mixture, thereby increasing the concentration of lower alkyl alcohol in the stripping mixture, separating the stripping mixture from the reaction mixture, compressing the stripping mixture to increase its pressure, cooling the stripping mixture to reduce its temperature, thereby condensing at least a first portion of the lower alkyl alcohol to a liquid, separating condensed lower alkyl alcohol from the stripping mixture to reduce the amount of lower alkyl alcohol in the stripping mixture to a range of from about 1 ppm to about 10,000 ppm, and directing the resulting stripping mixture to an expansion turbine in which the temperature and pressure of the stripping mixture are reduced, wherein energy resulting from the decrease in the stripping mixture temperature and pressure in the expansion turbine is used to compress the stripping mixture separated from the reaction mixture.

17. A method for synthesizing a polyol fatty acid polyester comprising the steps of:

(a) reacting a polyol and a fatty acid lower alkyl ester to produce a reaction mixture comprising polyol fatty acid polyester and lower alkyl alcohol, (b) contacting the reaction mixture with a stripping mixture comprising an inert stripping gas, up to about 10,000 ppm lower alkyl alcohol and up to about 2000 ppm oxygen, wherein at least a portion of the lower alkyl alcohol is transferred from the reaction mixture to the stripping mixture, thereby increasing the concentration of lower alkyl alcohol in the stripping mixture, (c) separating the stripping mixture from the reaction mixture, (d) compressing the stripping mixture to increase its pressure, (e) cooling the stripping mixture to reduce its temperature thereby condensing at least a first portion of the lower alkyl alcohol to a liquid, (f) separating condensed lower alkyl alcohol from the stripping mixture to reduce the amount of lower alkyl alcohol in the stripping mixture to a range of from about 1 ppm to about 10,000 ppm, and (g) directing the resulting stripping mixture to an expansion turbine in which the temperature and pressure of the stripping mixture are reduced, wherein energy resulting from the decrease in the stripping mixture temperature and pressure in the expansion turbine is used to compress the stripping mixture separated from the reaction mixture.

18. The method according to claim 17, wherein in step (e) the stripping mixture is passed through at least two heat exchangers having a coolant flowing therethrough which reduces the temperature of the stripping mixture to less than about −35° C.

19. The method according to claim 17, wherein the lower alkyl alcohol is methanol.

20. The method according to claim 18, wherein the stripping mixture exiting the expansion turbine is used as the coolant in at least one of the heat exchangers.

21. The method according to claim 1, wherein after step (f) the stripping mixture is passed through a demister to separate from the stripping mixture at least a portion of any entrained droplets of liquid.

22. The method according to claim 21, wherein the demister is a fiber mist eliminator.

23. The method according to claim 1, wherein the polyol fatty acid polyester is selected from the group consisting of esterified linked alkoxylated glycerins, esterified epoxide-extended polyols and mixtures thereof.

24. The method according to claim 1, wherein in step (d) the stripping mixture is passed through a heat exchanger having a coolant flowing therethrough which reduces the temperature of the stripping mixture to less than about −35° C.

25. The method according to claim 24, wherein said coolant is the stripping mixture exiting the expansion turbine.

26. The method according to claim 17, wherein in step (e) the stripping mixture is passed through a heat exchanger having a coolant flowing therethrough which reduces the temperature of the stripping mixture to less than about −35° C.

27. The method according to claim 26, wherein said coolant is the stripping mixture exiting the expansion turbine.

* * * * *